(12) United States Patent
Pogue et al.

(10) Patent No.: US 7,962,198 B2
(45) Date of Patent: Jun. 14, 2011

(54) SYSTEM AND METHOD FOR SPECTRAL-ENCODED HIGH-RATE HEMODYNAMIC TOMOGRAPHY

(75) Inventors: Brian William Pogue, Hanover, NH (US); Daqing Piao, Hanover, NH (US)

(73) Assignee: The Trustees of Dartmouth College, Hanover, NH (US)

( * ) Notice: Subject to any disclaimer, the term of this patent is extended or adjusted under 35 U.S.C. 154(b) by 1080 days.

(21) Appl. No.: 11/115,865

(22) Filed: Apr. 27, 2005

(65) Prior Publication Data
US 2006/0247531 A1 Nov. 2, 2006

(51) Int. Cl.
*A61B 6/00* (2006.01)
(52) U.S. Cl. .................................. 600/473; 600/310
(58) Field of Classification Search .......... 600/473–478, 600/309, 310
See application file for complete search history.

(56) References Cited

U.S. PATENT DOCUMENTS

| | | | | |
|---|---|---|---|---|
| 4,515,165 A * | 5/1985 | Carroll | | 600/475 |
| 5,349,954 A | 9/1994 | Tiemann et al. | | |
| 5,447,159 A * | 9/1995 | Schultz | | 600/477 |
| 5,692,511 A * | 12/1997 | Grable | | 600/425 |
| 5,694,938 A * | 12/1997 | Feng et al. | | 600/425 |
| 5,722,407 A | 3/1998 | Klingenbeck-Regn et al. | | |
| 6,195,580 B1 * | 2/2001 | Grable | | 600/473 |
| 6,324,418 B1 * | 11/2001 | Crowley et al. | | 600/476 |
| 6,615,063 B1 * | 9/2003 | Ntziachristos et al. | | 600/312 |
| 6,662,042 B1 * | 12/2003 | Grable | | 600/473 |
| 6,903,825 B2 * | 6/2005 | Tualle | | 356/450 |
| 7,047,057 B2 * | 5/2006 | Hall et al. | | 600/407 |
| 7,133,138 B2 * | 11/2006 | Horii et al. | | 356/497 |
| 7,231,243 B2 * | 6/2007 | Tearney et al. | | 600/407 |
| 7,383,076 B2 * | 6/2008 | Ntziachristos et al. | | 600/473 |
| 2003/0085338 A1 * | 5/2003 | Hall et al. | | 250/208.1 |
| 2003/0107742 A1 * | 6/2003 | Tualle | | 356/450 |

FOREIGN PATENT DOCUMENTS
WO    WO03012391 A    2/2003

OTHER PUBLICATIONS

Piao, D., Jiang, S., Srinivasan, S., Pogue, B. W., "Video-rate near-infrared optical tomography using spectrally-encoded parallel light delivery" (submitted to Optics Letters, 2005).

(Continued)

*Primary Examiner* — Sanjay Cattungal
(74) *Attorney, Agent, or Firm* — Lathrop & Gage LLP

(57) ABSTRACT

An optical tomography system has a group of lasers for generating light of multiple distinct wavelengths within a first wavelength band. Light from these lasers is directed into mammalian tissue at laser-specific locations on the tissue, and light from the mammalian tissue is collected at a plurality of reception points. Collected light from each reception point is separated according to its wavelength, and received by a photodetector to produce path attenuation signals representing attenuation along paths between the laser-specific locations on the tissue and the reception points. Image construction apparatus generates a tomographic image of heme concentrations in the mammalian tissue from the path attenuation signals. In an alternative embodiment, there is a second group of lasers operating in a second wavelength band, and the image construction apparatus can generate an image of heme oxygenation In the mammalian tissue.

19 Claims, 8 Drawing Sheets

OTHER PUBLICATIONS

Brooksby, B., Jiang, S., Kogel, C., Doyley, M., Dehghani, H., Weaver, J. B., Poplack, S. P., Pogue, B. W., Paulsen, K. D., "Magnetic Resonance-Guided Near-Infrared Tomography of the Breast" Review of Scientific Instruments, 75(12) 5262-5270 (2004).

Xu, H., Springett, R., Dehghani, H., Pogue, B. W., Paulsen, K. D., Dunn, J. F., An MRI-coupled Broad-band Near Infrared Tomography System for Small Animal Brain Studies Applied Optics, Apr. 10 Issue, (2005).

McBride, T. O., Pogue, B. W., Jiang, S. Österberg, U. L., Paulsen K. D., "A Parallel-detection frequency-domain near-infrared tomography system for hemoglobin imaging of the breast in vivo" Review of Scientific Instruments 72(3) 1817-24, Mar. 2001.

Pogue BW, McBride T. O., Osterberg U. L. and Paulsen K. D. "Comparison of imaging geometries for diffuse optical tomography of tissue." Opt Express 4(8), 270-286, 1999.

Pogue, B. W., Testorf, M., McBride, T., Osterberg,U., Paulsen, K. "Instrumentation and design of a frequency-domain diffuse optical tomography imager for breast cancer detection." Optics Express, 1(13), 394-403 (1997).

PCT/US2006/016210 International Search Report, mailed Dec. 18, 2006, 5 pages.

PCT/US2006/016210 International Preliminary Report on Patentability, mailed Nov. 8, 2007, 8 pages.

* cited by examiner

SYSTEM AND METHOD FOR SPECTRAL-ENCODED HIGH-RATE HEMODYNAMIC TOMOGRAPHY

STATEMENT REGARDING FEDERALLY SPONSORED RESEARCH

The United States Government has certain rights in this invention pursuant to contract number 1R21CA100984-01A1 awarded by the National Institutes of Health.

BACKGROUND

1. Field

The present application relates to the field of Near-Infrared (NIR) tomography for imaging mammalian tissue. This method introduces a method for imaging in parallel with multiple sources simultaneously activated.

2. Description of the Related Art

Visible light and near infrared radiation is absorbed by the Heme group of myoglobin and hemoglobin molecules. Further, the spectral characteristics of absorption by heme groups varies noticeably with their degree of oxygenation. Therefore, imaging mammalian soft tissues with visible and near-infrared wavelengths offers potentially high contrast between portions of the tissue containing high (such as blood and muscle) and low (such as fat) amounts of heme, and between highly oxygenated and poorly oxygenated or infarcted tissues.

As a result of the high vascularity in tumors, there is an elevated hemoglobin content and therefore potentially high intrinsic optical contrast between some tumors and normal tissue. This difference is especially pronounced in breast tumors where the stroma typically has low vascular density.

Imaging Heme

Visible light and near infrared light penetrate mammalian soft tissues to some degree. The usefulness of electromagnetic radiation of these wavelengths for imaging deep soft tissues has been limited because of the high degree of scattering that occurs, and resultant poor image quality with ordinary optical techniques.

Optical Tomography is a technique wherein tissue is illuminated with near-infrared or visible light at multiple source points on a tissue surface. Light transmitted through the tissue from each source point is then measured at each of multiple reception points on the tissue surface to measure attenuation and scattering along paths from each source point to each reception point. Parameters of a computerized tissue model are adjusted such that modeled tissue matches the measured attenuation and scattering along each path. The parameterized tissue model is then projected onto one or more hypothetical image planes, which are then prepared as images and displayed to a radiologist. Apparatus for optical tomography, similar to that described in C. H. Schmitz, M. Löcker, J. M. Lasker, A. H. Hielscher, and R. L. Barbour, "Instrumentation for fast functional optical tomography," Rev. Sci. Instr., 73(2): 429-439 (2002), has been marketed by NIRx Medical Technologies, LLC. of Glen Head, N.Y. The apparatus marketed by NIRx can resolve 5-millimeter lesions 3 centimeters below the skin surface.

The apparatus of Schmitz mechanically distributes light from a single laser into multiple illumination points spaced over the tissue to be studied in succession. As each illumination point is illuminated, light received at multiple reception points spaced over the tissue is measured. With the apparatus of Schmitz, data for approximately 3 image planes per second can be acquired.

Need for Speed

The amount of heme at a particular soft-tissue location can vary rapidly. For example, both elastic and muscular arteries, including associated pathology such as aneurysms, may enlarge and shrink with each heartbeat. Active muscle and brain tissue not only is known to consume oxygen at an activity-dependent rate, thereby changing its spectral characteristics, but releases local vasoactive substances such as adenosine; resulting activity-dependent vasodilation can occur in seconds. Vasculature in different tissue types, such as tumor and surrounding tissue, can also respond differently to exogenous vasoactive substances.

Similarly, since the corpora cavemosa may undergo rapid changes in heme content and oxygenation, imaging of those changes could be of interest in the study, diagnosis and treatment of erectile dysfunction or priapism.

The sometimes-rapid variations of heme distribution and oxygenation are referred to as the hemodynamics of the tissue.

With the optical tomography apparatus of Barbour, light is provided to one source point on the tissue surface at a time. After measuring received light from this source point at each reception point, the illuminated source point is changed. As a result, it can take significant acquisition time to gather sufficient path attenuation and scattering data to develop a high-resolution parameterized tissue model.

It is desirable to have short acquisition time to measure the dynamic aspects of heme distribution. It has been proposed that scattering and attenuation for multiple paths can be acquired simultaneously using intensity modulation encoding of the source. Franceschini (Francheschini et al, "Frequency-domain techniques enhance optical mammography: Initial clinical results" Proc Natl Acad Sci USA. 94(12): 6468-6473, 1997) demonstrated this approach with a frequency domain source, and the concept was further developed by Siegel (Siegel, A M, Marota, J J A and Boas, D A. "Design and evaluation of a continuous-wave diffuse optical tomography system." Optics Express 4:287-298, 1999) for a continuous wave source based system. Siegel developed a system where several source points are illuminated at the same time. Light applied to each simultaneously-illuminated source point is amplitude modulated in such that light from that source point can be distinguished from light applied to other simultaneously-illuminated source points, by having a different modulation frequency. For example, if one source point is amplitude-modulated with a first tone, and a second source point is amplitude-modulated with a second tone, light received at a reception point can be distinguished by measuring a ratio between the first and second tone in modulation as received at the reception point.

Tissue Oxygenation

Oxygenation of soft tissue is not always uniform. For example, in atherosclerotic disease, impaired blood flow may result in portions of tissue becoming ischemic, or having less than normal oxygen saturation, especially during activity.

The degree of oxygenation and heme content of soft tissue regions under varying conditions can be of interest to a physician attempting to diagnose disease. For example, it is known that many malignant tumors require so much oxygen that portions of the tumor may become ischemic and necrotic despite their increased vascularity. Much heart disease is ischemic, as are many strokes. Peripheral vascular disease, often implicated in diabetic foot ulcers, often produces—sometimes activity-dependent—inadequate blood flow and abnormal zones of ischemia in peripheral tissue such as limb tissue. These zones of ischemia tend to be more prone to forming slow or non-healing ulcers than normally oxygenated tissue. Accurate imaging of vessel obstructions and ischemia in tissue may allow more successful debridement of ulcers and permit success with other treatments such as revascularization.

Medically interesting images could also be obtained by observing changes in tissue heme concentration and oxygenation upon activity-induced release of vasoactive substances as well as changes induced by administration of exogenous vasoactive substances.

Imaging of rapid activity-dependent changes in regional distribution of heme content and oxygenation of brain tissue could be of interest in research into brain function as well as in the diagnosis of a wide variety of neurological conditions including epilepsy.

It is known that tissue oxygenation can be mapped by comparing a first optical tomographic image acquired using a light source of a first wavelength, with a second optical tomographic image acquired using a light source of a second wavelength. Differences between absorption at the first and second wavelength relate to tissue oxygenation as represented by a "color" of heme groups in the tissue.

It is therefore desirable to acquire data for tomographic images rapidly.

SUMMARY

In one embodiment, a tomographic system includes multiple source channels and multiple reception channels. Each source channel includes a light source producing light of a different wavelength than any other simultaneously active light source in the system, the light sources are separated from each other by a narrow wavelength separation. Each reception channel has the ability to measure the wavelength distribution of light received on that channel, as well as the light's overall amplitude. The wavelength distribution and amplitude on each reception channel is used to determine path attenuation and scattering information for each path between the source channels to reception channels. The source channels and reception channels are distributed along a surface of mammalian tissue.

The tomographic system also includes a processor for constructing an image of the target by processing path attenuation information.

In an alternative embodiment, the tomographic system includes source channels coupled to light source at two, widely separated, wavelengths. In an alternate embodiment of this embodiment, a first group of source channels operates at narrowly-separated wavelengths near a first wavelength, while a second group of source channels operates at narrowly-separated wavelengths near a second wavelength. The first and second wavelengths are widely separated. In this alternate embodiment, differences in attenuation at the first and second wavelengths are used to measure oxygenation of the mammalian tissue.

DETAILED DESCRIPTION

It has been found that the spectral characteristics of features within mammalian tissue are sufficiently broad that, if visible or near-infrared light from a group of single-mode lasers are used to interrogate tissue with small wavelength separation between lasers, radiation from each laser suffers levels of attenuation and scattering largely similar to radiation from the other lasers of the group.

When lasers at separate wavelengths are associated with different source positions, a spectral encoding of source origin occurs in a way that can be detected and decoded in parallel at any reception point.

Figure 1:
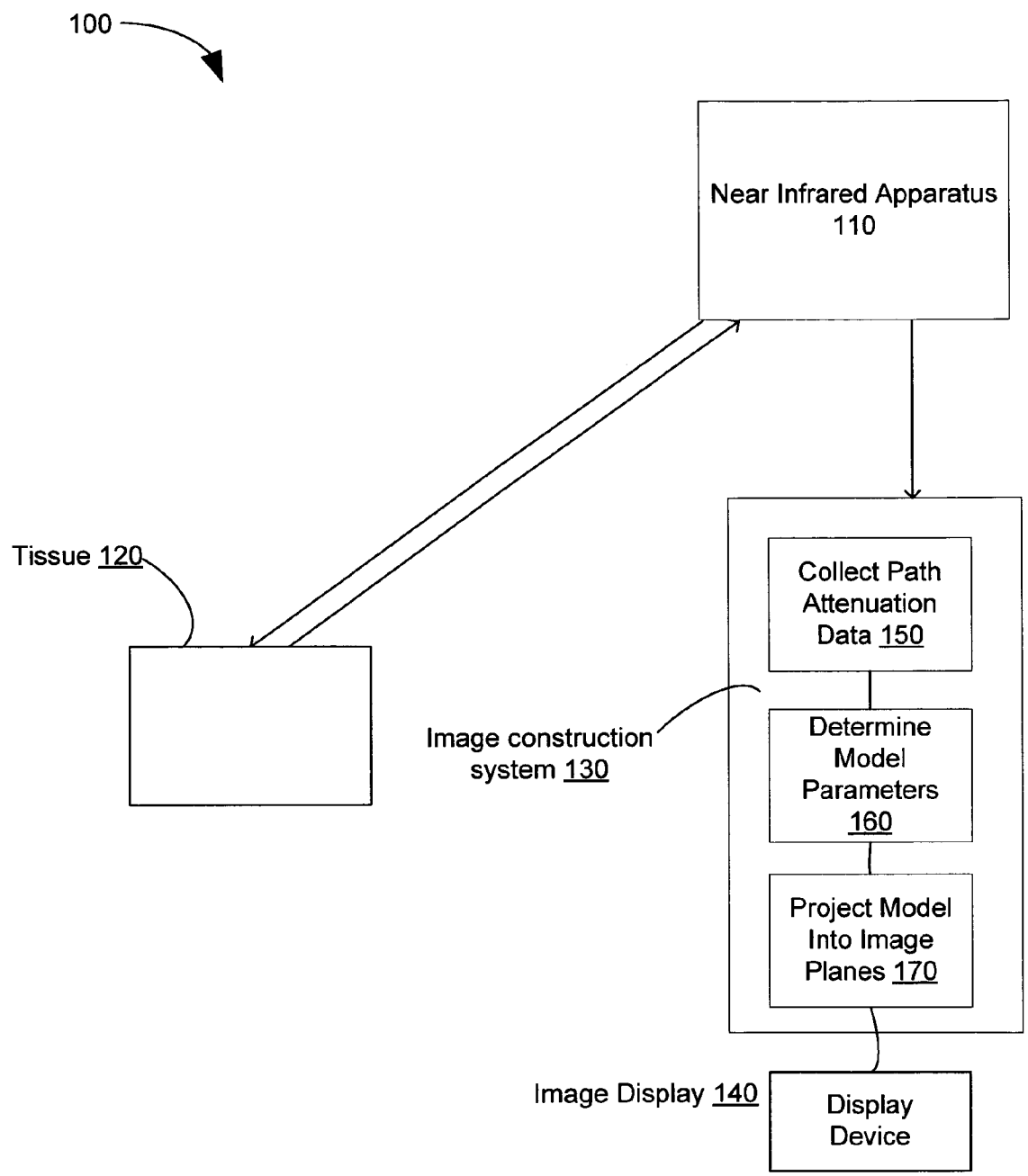
FIG. 1 is a block diagram of a system of Spectral-Encoding for High-Rate Hemodynamic Tomography.

FIG. 1 shows a System 100 of Spectral-Encoding for High-Rate Hemodynamic Tomography. The System 100 includes a near-infrared apparatus 110, mammalian tissue 120, an image construction system 130, and an image display 140. A tissue model, or phantom, may be used in place of tissue 120 during development and calibration. The near-infrared apparatus 110 generates path-attenuation data 150 from tissue 120. The image construction system 130 is configured to receive the path-attenuation data 150 from the near-infrared apparatus 110 and construct an image of the tissue 120 on the image display 140. The image construction system 130 collects tissue-dependent path attenuation data 150 from the near-infrared apparatus 110, determines voxel attenuation parameters of a tissue model 160, and projects 170 the voxel attenuation parameters into tomographic image planes to generate tomographic images for display on the image display 140 using algorithms known in the art. Images are also recorded for later study.

Figure 2:
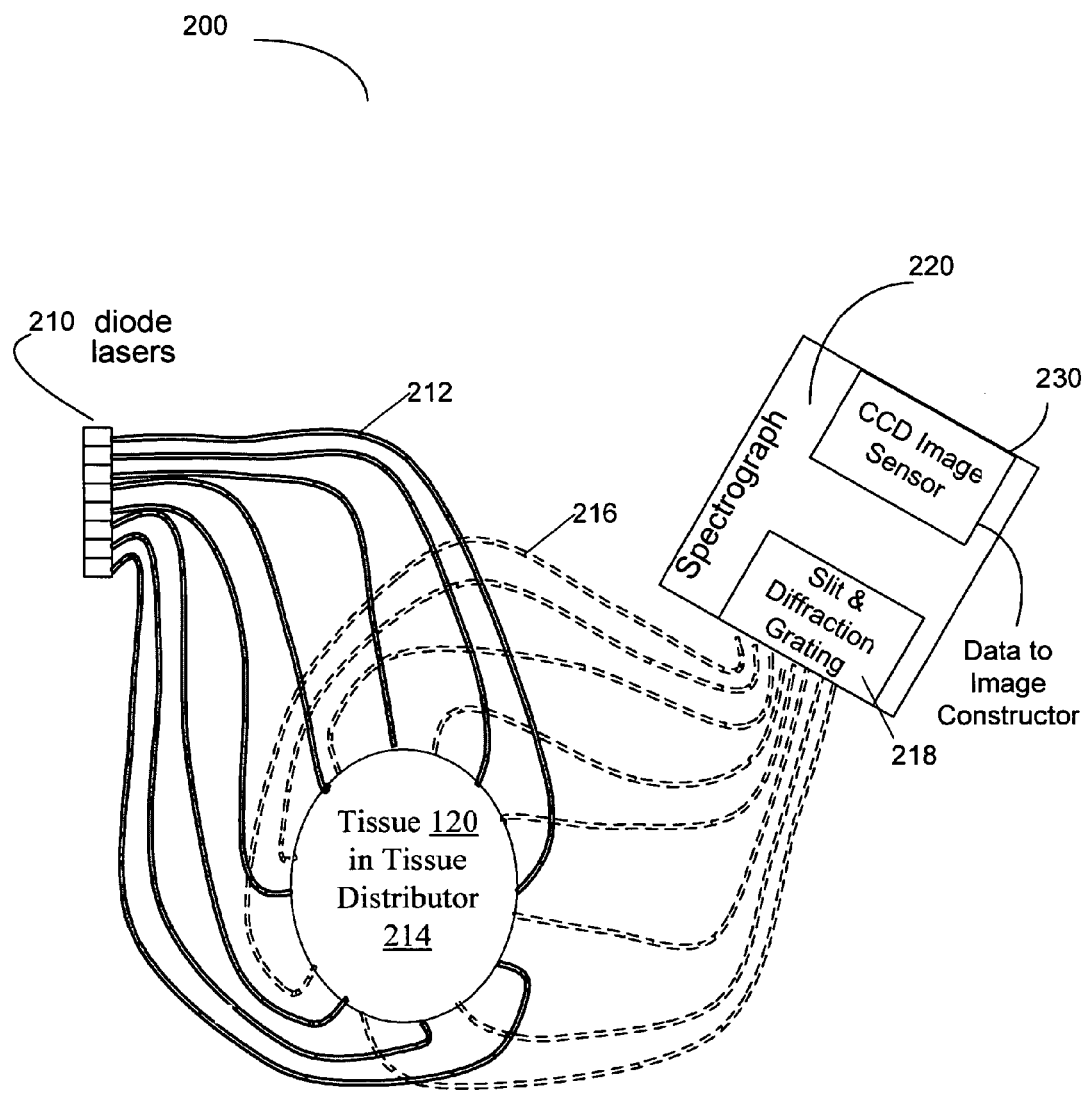
FIG. 2 is a simplified block diagram of a near-infrared apparatus of FIG. 1.

FIG. 2 is an abbreviated schematic 200 of the near infrared apparatus 110 of FIG. 1. In an embodiment, near infrared apparatus 110 includes eight diode lasers 210, a spectrograph 220 and a CCD 230. Spectral encoding of diode lasers is achieved by using a number of lasers each operating upon a distinct wavelength in the same spectral band, preferably spaced 0.5 to 1 nm apart within a 4 nm to 10 nm nominal bandwidth band. It is anticipated that tighter laser spacing will be used in future versions of the apparatus, especially in embodiments having more lasers. Each diode laser of the eight diode lasers 210 illuminates the tissue 120 at laser-specific locations through transmit optic fibers 212 and tissue distributor 214 simultaneously. Light from each laser of lasers 210 is applied at a different location along the periphery of tissue.

Light from lasers 210 penetrates the tissue 120. Some of this light is absorbed in the tissue, some is scattered. Light is received from tissue 120 through tissue distributor 214 and receive optic fibers 216 into spectrometer 220. The optic fibers 216 are arranged along the light entry slit 218 of spectrograph 220, such that light from each fiber 216 enters at a separate location along the slit. Light admitted through the entry slit 218 passes through a diffraction grating, and is spread into its spectral components as it is projected onto a charge-coupled device (CCD) image sensor 230 array. Signals from CCD image sensor 230 go to image construction system 130. Signals from CCD image sensor 230 encode received light amplitude for each reception point at each wavelength corresponding to each laser of lasers 210.

Light from each receive optic fiber 216 may, and often does, include light scattered through tissue 120 from more than one of lasers 210. Since lasers 210 operate on separate wavelengths, the diffraction grating of spectrograph 220 separates these wavelengths, such that light received from each laser 210 through each receive optic fiber 216 illuminates a separate location on CCD image sensor 230, where it illuminates several photodetector elements of CCD image sensor 230.

Figure 3:
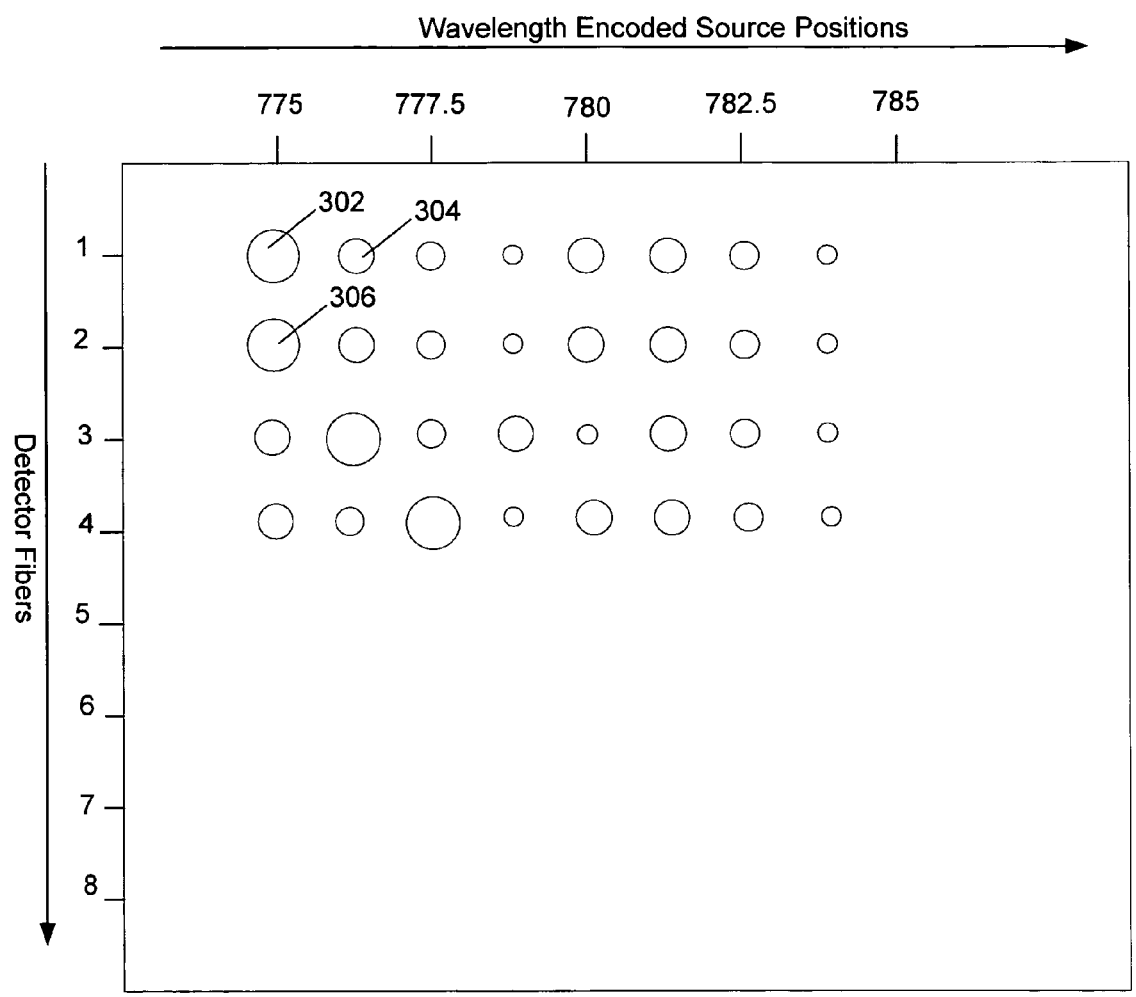
FIG. 3 is a schematic image of the light intensities viewed by a CCD chip of the near-infrared apparatus of FIG. 2.

Since light from each receive optic fiber 216 enters spectrograph 220 at a separate location along entry slit 218, the CCD is illuminated with a light pattern similar to that illustrated in FIG. 3. Light originating at a first laser of lasers 210 and received through a first fiber 216 arrives at location 302. Light received through the first fiber 216 but originating from a second laser of lasers 210 arrives at a second location 304, and light originating from the first laser of lasers 210 and received through a second fiber of fibers 216 arrives at a third location 306 on the CCD. While this received light pattern is used by image construction system 130 to construct an image of tissue 120, the received light pattern is not directly an image of tissue 120.

In an embodiment, CCD image sensor 230 has an array of 512 by 512 separate sensor elements, each capable of transducing near infrared or visible light into a signal, signals from the separate sensor elements correspond to path attenuation information and are encoded into a CCD output signal for use by image construction system 130. It is anticipated that the present apparatus will function with CCD image sensors of other array sizes, particularly those having a greater number of sensor elements.

For monochrome imaging of heme concentration, it is desirable that each laser of lasers 210 be close, preferably within one percent, to a center wavelength so that scattering of each laser is similar to the other lasers. It is also desirable that the center wavelength be close to 800-810 nanometers (nm) wavelength, because at this wavelength heme light absorption is similar for oxygenated and for unoxygenated hemoglobin. Useful images are obtainable if the center wavelength lies between 650 and 900 nm.

In a particular embodiment, each laser of lasers 210 is within the wavelength band of 775.0 to 785.0 nm, hence its bandwidth is less than one and a half percent of its center wavelength, but are spaced apart in that band by approximately 1.2 nm, and are within fifty nm of 800-810 nm. In an embodiment, the diode lasers 210 are capable of 50 mW each. The lasers are mounted on thermoelectric coolers such that laser operating wavelengths are stable.

In near-infrared apparatus 110 a spatially-varying neutral density filter is interposed between lasers 210 and transmit fibers 212 to even out the intensity of illumination, compensating for variations in laser power. Similarly, a spatially-varying neutral density filter is interposed between receive fibers 216 and slit 218 to compensate for variations in receive fiber coupling from tissue 120.

In an alternative embodiment, not shown, there are sixteen receive fibers 216 instead of the eight previously discussed. It is anticipated that the present apparatus is operable with, and may provide improved resolution with, other and greater numbers of receive fibers.

It has been found that sufficient data for images of rodent crania can be acquired in 10 milliseconds while operating the lasers at 10 mw. It is anticipated that imaging oxygen saturation and heme concentration of human brain cortex may require operation at between 1-100 mWatts, for 10 to 50 ms. These capture times can support imaging at video rates.

Specific applications in which the system could be used are in imaging blood pulsation in tissue, to assess disease or response to therapy. Monitoring uptake or retention of drugs which are optically absorbing or scattering can also be utilized. Other applications that come to mind include detection of epidural and subdural hematomas and active intracranial bleeding. Also, it is possible to use the system for imaging of breast tumors and response of the tumor to external stimuli such as different breathing gases, applied pressure, vascular flow changes. Imaging fast temporal changes in blood flow in response to an injected drug could be a human application, such as monitoring peripheral vascular disease response to a drug, or tissue ischemia response to a drug. The uptake and wash out of vascular or tissue maker drugs could also be a human application.

For imaging of heme oxygenation as well as heme concentration, it is desirable that there be two groups, a short wavelength group and a long wavelength group, of illumination source lasers. Lasers of each group should operate at a wavelength near to a center wavelength of the group. Both groups of lasers should operate in the 650 to 900 nanometer band, but the center wavelengths for the groups should be spaced apart. Spacing the center wavelengths between five and fifteen percent wavelength apart will provide resolution of oxygenation.

Figure 4:
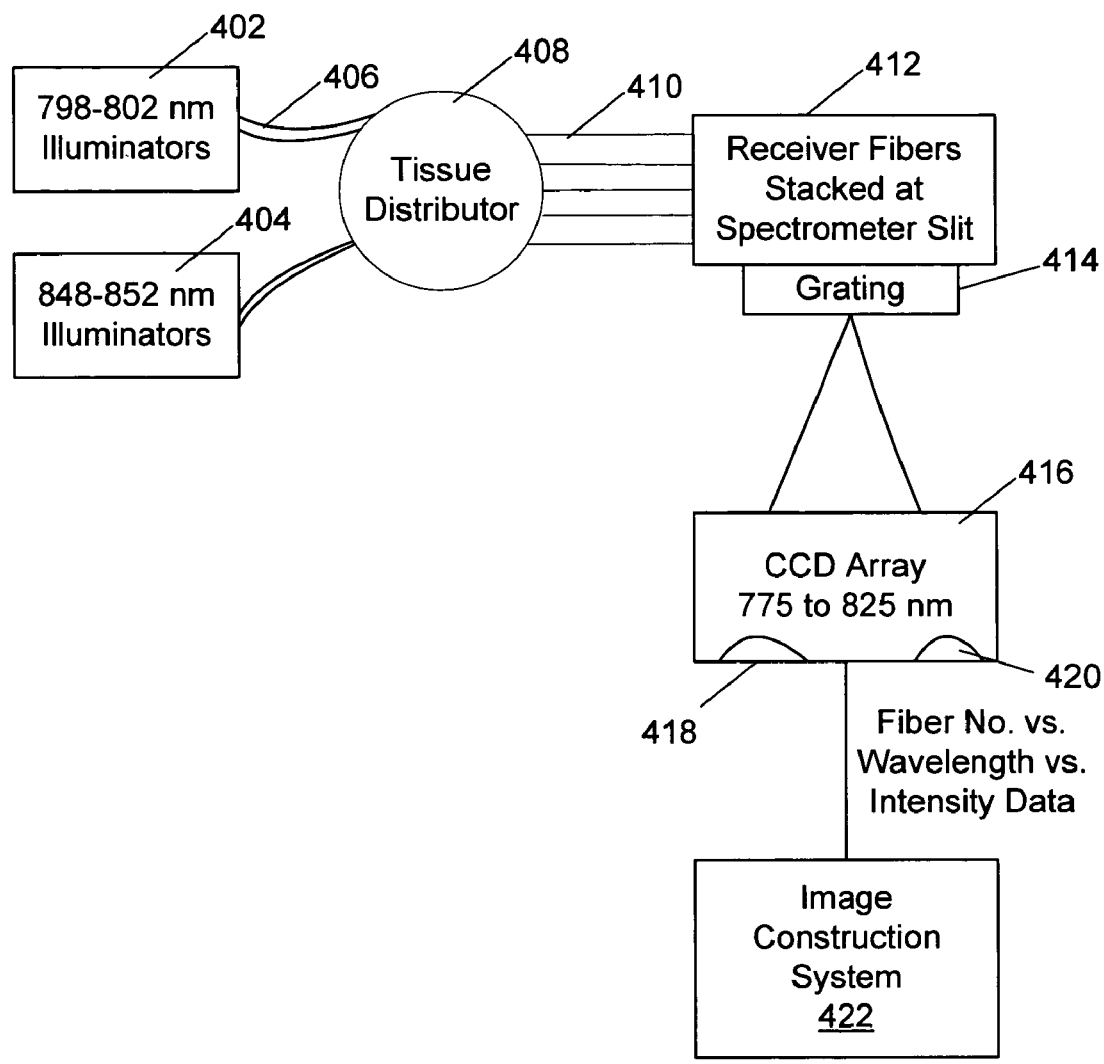
FIG. 4 is a block diagram of a system according to an alternative embodiment for imaging oxygen saturation.

In another, dichrome, embodiment as illustrated in FIG. 4, suitable for imaging oxygen saturation in tissue as well as heme concentration in tissue, there are eight diode lasers of a first group 402 having wavelengths spaced in the band from 775 to 780 nm, spaced approximately 0.5 nm apart, and eight diode lasers of a second group 404 having wavelengths spaced 0.5 nm apart in the band of 820 to 825 nm. The center wavelengths of the first group and center group are therefore separated by approximately six percent, between five and fifteen percent, and each group is less than one percent wide.

Near-infrared light from the diode lasers of both groups 402, 404 is coupled through transmit fibers 406 and tissue distributor 408 into mammalian tissue under study. Light from the mammalian tissue under study is coupled from tissue distributor 410 through receive fiber 410 into spectrometer slit 412 and the spectrometer diffraction grating 414. After passage through the diffraction grating 414, the light is projected onto a CCD sensor array 416. The light originating in the first group of lasers 402 arrives at laser-and-reception fiber-specific locations in a first region 418 of the CCD sensor array 416. The light originating in the second group of lasers 404 arrives at laser-and-reception fiber-specific locations in a second region 420 of the CCD sensor array 416. The CCD sensor array 416 is periodically scanned, pixel exposure information is digitized, and the digitized data is transferred to an image construction system 422. In this embodiment, CCD sensor array 416 is a 2048 by 1024 pixel array. It is anticipated that filters are provided to reduce sensitivity of the apparatus to stray incident light, such as visible light, outside the band of interest.

Image construction system 422 receives digitized data from the CCD 416 and uses information from the first region 418 of the array to construct an image of heme of a first "color". Image construction system 422 also uses information from the second region 420 of the CCD 416 to construct an image of heme of a second "color". At any one region of mammalian tissue, the ratio of light absorption by heme in one band to absorption by heme in the second band is dependent upon oxygen saturation of heme in that region of tissue. The first "color" and second "color" images are therefore compared to produce an image of oxygen saturation in various portions of the tissue present in the tissue distributor 408.

In an alternative embodiment, two CCD sensor arrays are used, one receives light originating in the first group of lasers 402, the second receives light originating in the second group of lasers.

Figure 5:
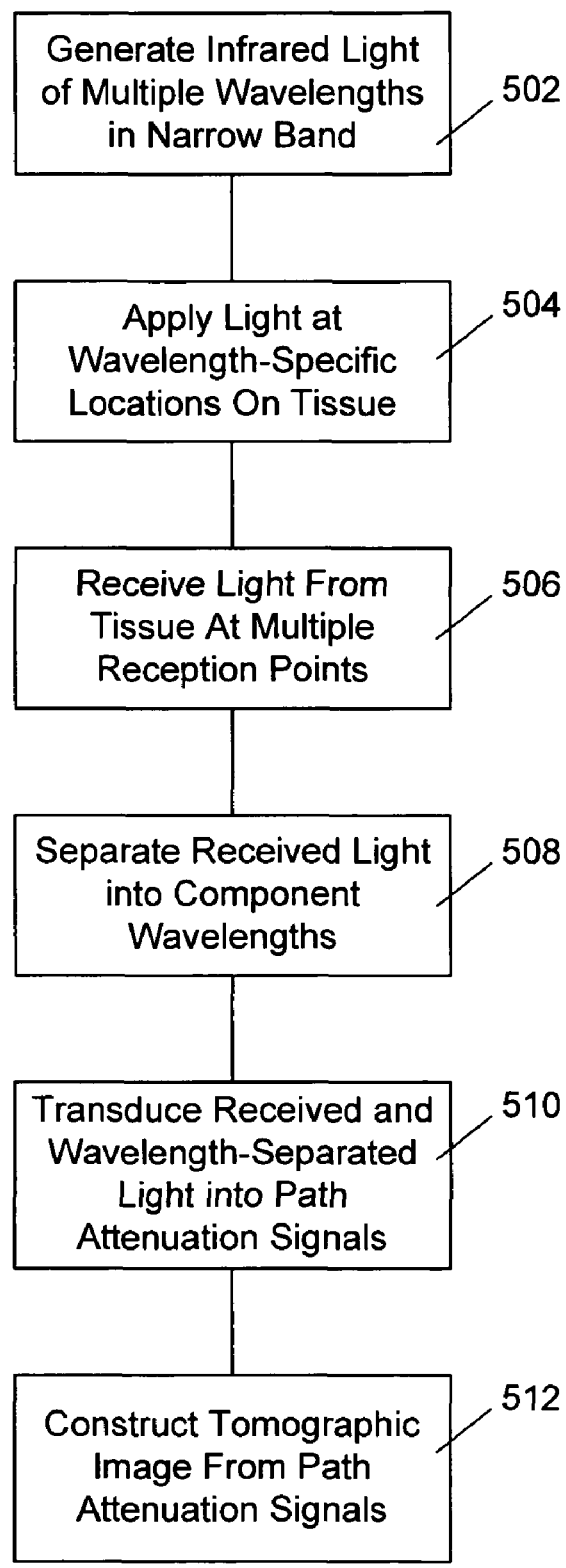
FIG. 5 is a flowchart illustrating a method for Spectral-Encoding for Video-Rate Hemodynamic Tomography.

FIG. 5 illustrates a flowchart of the method for constructing tomographic images of heme concentrations in tissue. With reference to FIG. 1 and FIG. 2, near-infrared apparatus 110 includes a group of laser light sources 210 for generating 502 infrared light of laser-specific wavelengths in a narrow band of wavelengths. Light from these lasers is collected and applied 504 to mammalian tissue 120 through transmit fibers 212 and tissue distributor 214, then light from tissue 120 is received 506 through tissue distributor 214 and receive fibers 216 at multiple reception points on tissue 120.

Light received 506 from tissue is separated 508 by spectrometer 220 according to wavelength of its components, each wavelength corresponding to a specific laser of laser light sources 210, while maintaining separation according to receive point. This light is transduced 510 by CCD sensor 230 into electronic signals corresponding to path attenuation.

The electronic signals corresponding to path attenuation are input to an image construction system 130, where a tomographic image of the tissue is constructed 512 as previously described.

Figure 6:
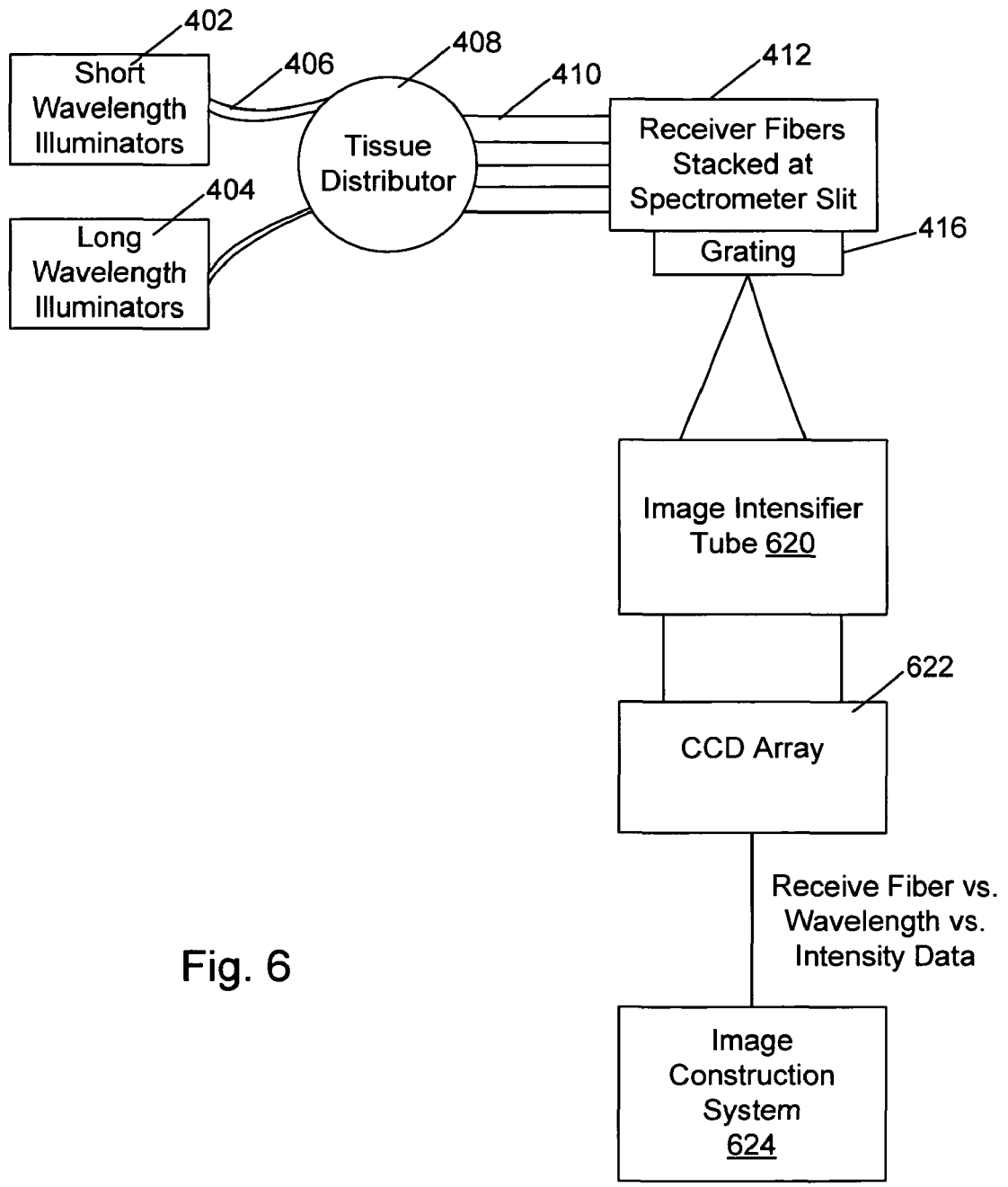
FIG. 6 is a block diagram of an embodiment incorporating an image intensifier tube for improved weak-signal gain.

It can be desirable to have high photodetector gain when imaging structures deep in mammalian tissue. The embodiment illustrated in FIG. 6 is an alternative embodiment having a front-end as previously described with reference to FIG. 4. In this embodiment, received infrared light transiting the diffraction grating 416 impinges not directly upon the CCD image sensor 418 of FIG. 4, but upon the photocathode of a third-generation image intensifier tube 620. Light from the image intensifier's luminescent anode projects onto a CCD image sensor 622. Data indicative of received intensity at each wavelength and reception fiber is encoded and transmitted to the image construction processor 624.

Figure 7:
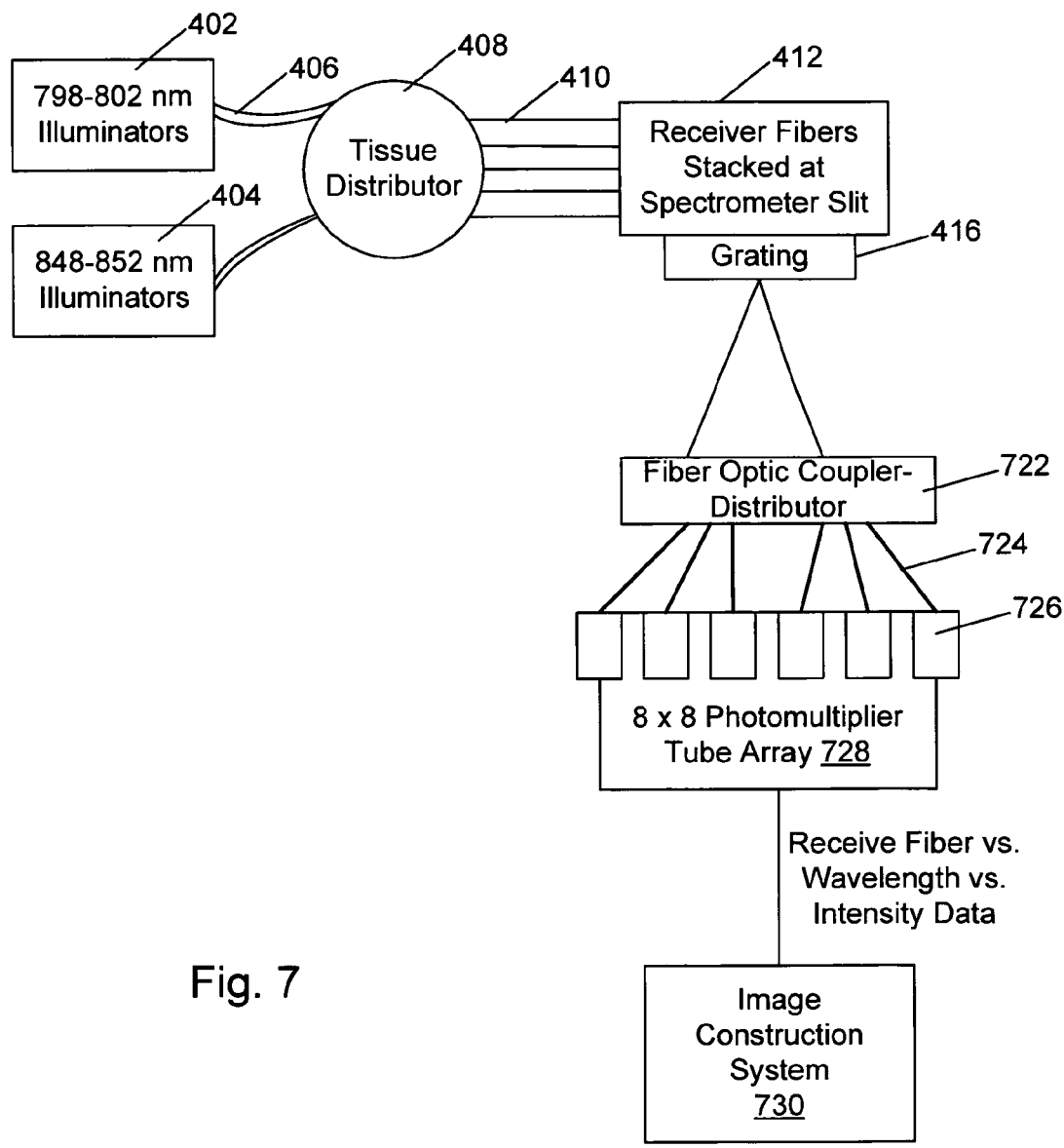
FIG. 7 is a block diagram of an embodiment incorporating a fiber-optic distributor and an array of photomultiplier tubes for improved weak-signal gain.

The embodiment illustrated in FIG. 7 is an alternative embodiment having a front-end as previously described with reference to FIG. 4. In this embodiment, received infrared light transiting the diffraction grating 416 impinges not directly upon the CCD image sensor 418, but upon the fibers of a fiber-optic coupler and distribution apparatus 722. Fiber-optic coupler and distribution apparatus 722 distributes light received from each combination of receive fiber 410 and wavelength through distribution fibers 724 into a separate photomultiplier tube 726 of photomultiplier tube array 728. In a monochrome embodiment, photomultiplier tube array 728 is an eight by eight (64-tube) array, while in a dichromatic embodiment, photomultiplier tube array 728 is a 128-tube array. Data from the photomultiplier tube array 728 indicative of received intensity at each wavelength and reception fiber is encoded and transmitted to the image construction processor 730.

Figure 8:
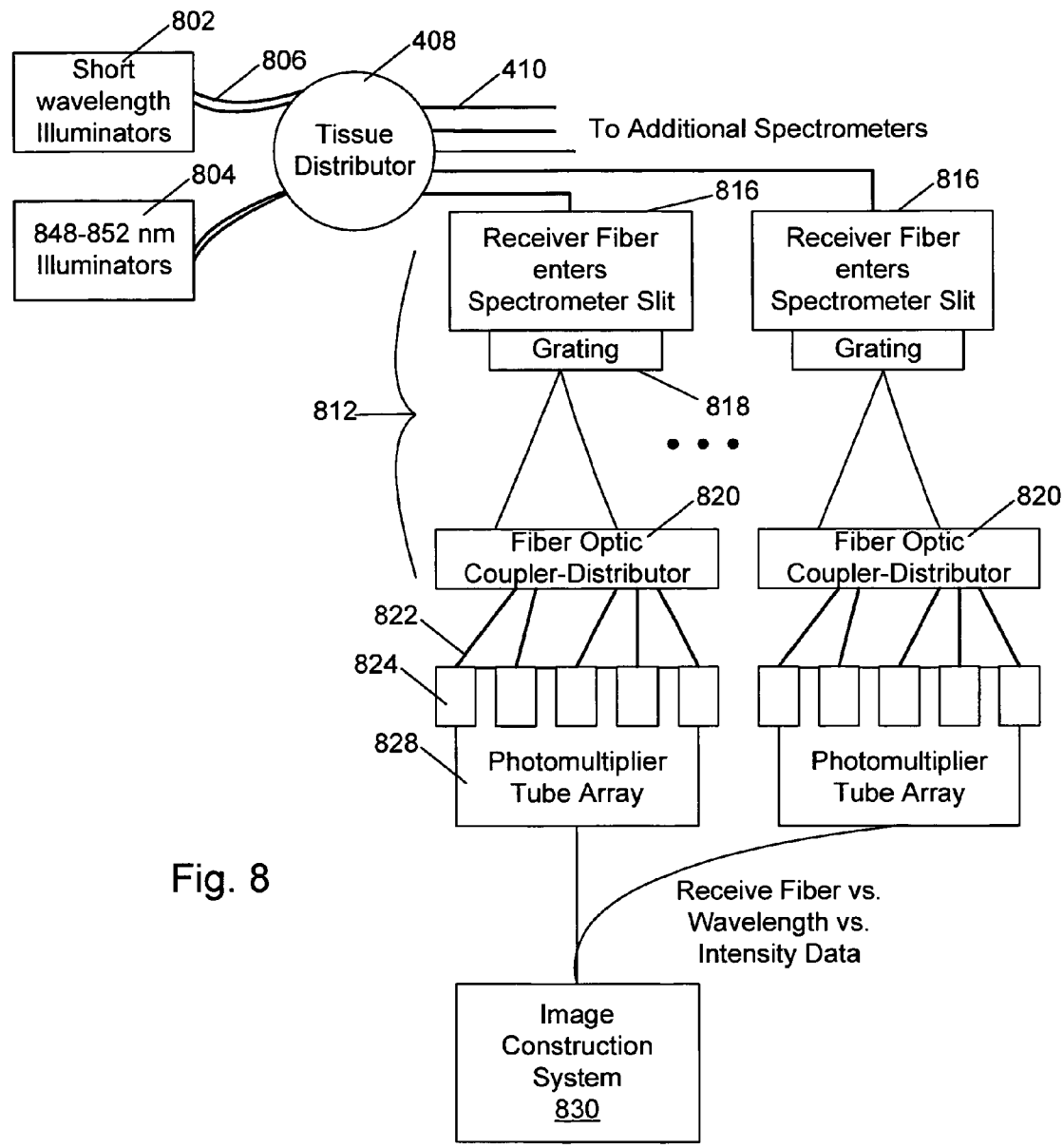
FIG. 8 is a block diagram of an alternative embodiment incorporating multiple spectrometers with an array of photomultiplier tubes.

The embodiment illustrated in FIG. 8 is an alternative embodiment having a front-end of short-wavelength lasers 802, long wavelength lasers 804, transmit fibers 806, and tissue distributor 808 as previously described with reference to FIG. 4. Receive fibers 810, however, distribute received light to multiple spectrometers 812, such that each receive fiber feeds one spectrometer 812. In this embodiment, received infrared light from at least one receive fiber enters a slit 816 of each spectrometer, then transits the associated diffraction grating 818. This light is projected upon fibers of a fiber-optic coupler and distribution apparatus 820 for each spectrometer 812. Fiber-optic coupler and distribution apparatus 820 distributes light received from wavelength associated with a illumination lasers 802, 804 through distribution fibers 822 into a separate photomultiplier tube 824 of photomultiplier tube array 828. In a monochrome embodiment, photomultiplier tube array 828 is an eight tube array for each spectrometer, in a dichrome embodiment photomultiplier tube array 828 is a 16-tube array for each spectrometer. Data from the photomultiplier tube arrays 828 of all eight spectrometers 812, indicative of received intensity at each wavelength and reception fiber, is encoded and transmitted to the image construction processor 830.

It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A tomography system, comprising:
    a plurality of lasers of a first group, each laser of the first group for generating light of a distinct wavelength within a first wavelength band;
    a plurality of lasers of a second group, each laser of the second group for generating light of a distinct wavelength within a second wavelength band not overlapping the first wavelength band,
    apparatus for applying the light from the lasers to mammalian tissue such that light from lasers of the first group is applied to the tissue at a plurality of laser-specific, spatially separated, first locations simultaneously and light from lasers of the second group is applied to the tissue at a plurality of laser-specific, spatially separated, second locations;
    apparatus for collecting light from the mammalian tissue at a plurality of reception points;
    a spectrographic device for separating light received from the apparatus for collecting light according to a wavelength of the received light, the light being spatially separated according to wavelength;
    apparatus for generating a path attenuation signal, the path attenuation signal encoding received light amplitude information for each reception point at each wavelength corresponding to each laser of the plurality of lasers of the first and second groups of lasers wherein the path attenuation signals corresponding to lasers of the first group are determined by a method comprising identifying light received from each laser of the first group by wavelengths of the lasers in the first group and path attenuation signals corresponding to lasers of the second group are determined by a method comprising identifying light received from each laser of the second group by wavelengths of the lasers of the second group; and
    image construction apparatus for receiving the path attenuation signal and for reconstructing a tomographic image of the mammalian tissue representative of oxygenation of the mammalian tissue and of attenuation by the mammalian tissue;
    and wherein the image construction apparatus is capable of generating an image corresponding to oxygenation of the mammalian tissue based upon differences in attenuation in tissue between light from lasers of the first group and from lasers of the second group.

2. The tomography system of claim 1, the apparatus for generating a path attenuation signal comprising a charge-coupled-device image sensor, and the spectrographic device for separating light being configured and arranged to project received light onto locations of the image sensor according to a wavelength of the received light.

3. The tomography system of claim 1 wherein the first locations are the same as the second locations.

4. The tomography system of claim 1 wherein the first wavelength band is of bandwidth less than one percent, and a center wavelength of the first wavelength band is separated from a center wavelength of the second wavelength band by between five and ten percent.

5. The tomography system of claim 4 wherein:
the spectrographic for separating light comprises a diffraction grating; and
the apparatus for generating a path attenuation signal comprises a fiber-optic distributor and a plurality of photomultiplier tubes.

6. The tomography system of claim 4 wherein:
the first wavelength band is within the range 750 to 860 nanometers
the spectrographic device for separating light comprises a diffraction grating; and
the apparatus for generating a path attenuation signal comprises a charge-coupled device (CCD) image sensor.

7. The tomography system of claim 6 wherein the apparatus for generating a path attenuation signal further comprises an image intensifier tube for amplifying light separated according to wavelength by the diffraction grating and for providing amplified light to the CCD image sensor.

8. The tomography system of claim 1 wherein the first wavelength band is near-infrared between 650 and 900 nanometers wavelength.

9. The tomography system of claim 8 wherein the first wavelength band is within the range 750 to 860 nanometers.

10. The tomography system of claim 8 wherein the first wavelength band is of bandwidth less than one and a half percent of its center wavelength.

11. The tomography system of claim 10 wherein:
the spectrographic device for separating light comprises a diffraction grating; and
the apparatus for generating a path attenuation signal comprises a charge-coupled device (CCD) image sensor.

12. The tomography system of claim 10 wherein:
the spectrographic device for separating light comprises a diffraction grating; and
the apparatus for generating a path attenuation signal comprises an image intensifier tube, and a charge-coupled device (CCD) image sensor.

13. The tomography system of claim 10 wherein:
the spectrographic device for separating light comprises a diffraction grating; and
the apparatus for generating a path attenuation signal comprises a fiber-optic distributor and a plurality of photomultiplier tubes.

14. A method of generating tomographic images of mammalian tissue comprising:
generating infrared light of a plurality of laser-specific wavelengths in a first narrow band of wavelengths;
generating infrared light of a plurality of laser-specific wavelengths in a second narrow band of wavelengths;
applying the infrared light to a plurality of spatially separated, laser-specific, stimulus locations on the mammalian tissue simultaneously, each laser-specific stimulus location transmitting one generated light of one wavelength in the first narrow band and one wavelength in the second narrow band;
receiving infrared light from a plurality of reception points on the mammalian tissue;
using a spectrographic device to separate received light from each reception point of the plurality of reception points according to wavelength into separated received light;
transducing the separated received light into electronic path attenuation signals, the path attenuation signals encoding received light amplitude information at each laser-specific wavelength as received at each reception point, the path attenuation signals corresponding to attenuation for each band along paths for light from each stimulus location to each reception point; and
constructing a tomographic image representative of tissue oxygenation and attenuation in the mammalian tissue from the electronic signals, the representation of tissue oxygenation based upon differences between absorption along paths associated with wavelengths of the first narrow band and along paths associated with wavelengths of the second narrow band.

15. The method of claim 14 wherein the first narrow band of wavelengths is less than two percent wide, and is in the near-infrared between 650 and 900 nanometers.

16. The method of claim 14 wherein the step of using a spectrographic device to separate received light is performed with apparatus comprising at least one diffraction grating.

17. The method of claim 14 wherein the second narrow band of wavelengths has a center wavelength differing from a center wavelength of the first narrow band of wavelengths by between five and fifteen percent.

18. The method of claim 14 wherein the step of transducing the separated received light is performed with apparatus comprising a charge-coupled-device (CCD) image sensor.

19. The method of claim 18 wherein the apparatus comprising a CCD image sensor further comprises an image intensifier tube for amplifying the separated received light.

* * * * *